United States Patent [19]

Klein et al.

[11] 4,318,831
[45] Mar. 9, 1982

[54] POLYSUBSTITUTED CYCLOPENTENE DERIVATIVES

[75] Inventors: Erich Klein; Ernst J. Brunke, both of Holzminden, Fed. Rep. of Germany

[73] Assignee: Dragoco Gerberding & Co GmbH, Holzminden, Fed. Rep. of Germany

[21] Appl. No.: 48,731

[22] Filed: Jun. 15, 1979

[30] Foreign Application Priority Data

Jun. 26, 1978 [DE] Fed. Rep. of Germany ....... 2827957

[51] Int. Cl.³ .................. A61K 7/46; C07C 33/12; C07C 69/007
[52] U.S. Cl. ................ 252/522 R; 560/231; 568/446; 568/838
[58] Field of Search ............... 252/522 R; 568/838, 568/446, 837, 667; 560/231

[56] References Cited

U.S. PATENT DOCUMENTS

| | | | |
|---|---|---|---|
| 3,937,723 | 2/1976 | Schulte-Elte | 568/838 |
| 4,052,341 | 10/1977 | Naipawer et al. | 568/838 |
| 4,069,258 | 1/1978 | Hoffmann et al. | 568/838 |
| 4,149,020 | 4/1979 | Kamath | 568/838 |
| 4,219,451 | 8/1980 | Yoshida et al. | 568/838 |

FOREIGN PATENT DOCUMENTS 1922391 8/1970 Fed. Rep. of Germany .

OTHER PUBLICATIONS

Aulchenko et al., "American Perfumer & Cosmetics", vol. 85, Jul. 1970, pp. 37–45.

Ohloff, "Fortschritte Chemischer Forschung", 12/2, (1969), pp. 212–215.
King et al., "J. Org. Chem.", vol. 26 (1961), pp. 326–329.
Isler et al., "Helv. Chim. Acta", vol. 40, pp. 1242–1249, (1957).
Trippett, "Quarterly Reviews", vol. 17, pp. 406–440, (1963).
Satsumabayashi et al., "Bul. Chem. Soc. Japan", vol. 43, (1970), pp. 1886–1888.

Primary Examiner—Werren B. Lone
Attorney, Agent, or Firm—Browdy and Neimark

[57] ABSTRACT

Polyunsaturated cyclopentane derivatives of the general formula

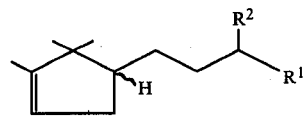

wherein $R^1$ signifies a lower alkyl group with 1 to 3 carbon atoms and $R^2$ signifies a hydroxymethyl, acetomethyl, or formyl group, and the wavy line on carbon atom 1 signifies epimeric forms have excellent aromatic properties and may be used in perfume compositions. The compounds in which $R^2$ is hydroxymethyl have a pronounced sandalwood scent. Methods of production are also disclosed.

3 Claims, 1 Drawing Figure

POLYSUBSTITUTED CYCLOPENTENE DERIVATIVES

FIELD OF THE INVENTION

The present invention concerns new substituted cyclopentene derivatives of the general formula I,

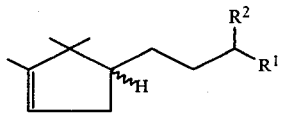

wherein $R^1$ signifies a lower alkyl group with 1 to 3 carbon atoms, $R^2$ signifies a hydroxymethyl, acetoxymethyl, or formyl group, and the wavy line on carbon atom 1 signifies epimeric forms.

The present invention also concerns the use of compounds of the general formula I as perfumes and also as perfume compositions, characterized by a content of a compound of the general formula I, as well as the preparation of such compounds. It has been found that the new polysubstituted cyclopentene derivatives of the general formula I are useful and stable perfumes. In particular, the derivatives with saturated side chains, wherein $R^1$=methyl, ethyl, or n-propyl and $R^2$=hydroxymethyl, have a pronounced sandalwood scent.

BACKGROUND OF THE INVENTION

The sandalwood oil from the East Indies used frequently in the perfume industry contains primarily the sesquiterpenes α-and β-santalol (A and B respectively), which also produce the characteristic mild woody odor of the oil.

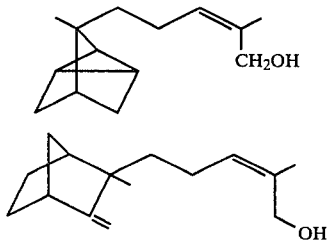

The limited availability and the high price of sandalwood oil motivated the development of chemical syntheses for A and B, which nevertheless could not be utilized industrially. The replacement products used currently are chiefly terpenylcyclohexanols (review article: I. S. Aulchenko and L. A. Kheifits, *American Perfumer and Cosmetic*, 37 (1970), which are obtained by an acid-catalyzed reaction of camphene with phenol derivatives and subsequent catalytic hydrogenation. Complex mixtures are thereby formed, which consist only to a small extent of active perfumes of the sandalwood type, and are frequently contaminated with terpenylphenols.

It would be natural to assume that the production of the most natural sandalwood scent possible would be expected from compounds which are structurally similar to the santalols A and B shown above, and which have a comparable molecular size or number of carbon atoms. However, this implies the synthesis of a comparatively complex ring system which, as shown above, requires complicated procedures and purification steps, or the introduction of comparatively long side chains with appropriate partial structure into a simpler skeletal structure. In the latter process, the results showed little success with respect to the shades of odor (review article: G. Ohloff, *Fortschr. Chem. Forsch.*, Vol. 12/2, page 212, 1969). Thus, in U.S. Pat. No. 4,052,341, besides higher-molecular-weight compounds or those with longer chains, the compound 3-methyl-5-(2,2,3-trimethylcyclopent-3-ene-1-yl)pentane-2-ol, a compound in which a rather long side chain containing a secondary hydroxyl group is bonded to the simple trimethylcyclopentene ring skeleton, is also shown. The process specified for industrial preparation of this substance produces a mixture of isomers which contains a large fraction of 6-(trimethylcyclopent-3-ene-1-yl)hexane-3-ol, so that the odor intensity and quality of the products are somewhat less satisfactory. The patent mentioned states that longer chains with secondary hydroxyl groups must be introduced in order to obtain the desired notes or shades of odor.

German Offenlegungsschrift No. 1,922,391 describes campholenylidenealkanols, namely campholenylidenepropanol, 2-campholenylidenebutanol and campholenylideneisopropanol, which have shades of fragrance reminiscent of musk, sandalwood, or of the aroma of figs. The disadvantage of these compounds too is that, because of the unsaturation in their side chains, as is frequently the case with such unsaturated compounds, they are chemically less stable, they have a tendency toward aging reactions, and are therefore less well suited as perfumes.

SUMMARY OF THE INVENTION

It has now been surprisingly found that the saturated partial structure with a primary hydroxyl group (1-hydroxy-2-methyl-alkanyl) of the santalols also produces excellent fragrances in combination with the trimethylcyclopentene skeleton, when shorter side chains are introduced, and the total number of carbon atoms in the compound is therefore reduced. Thus, the compound 4a FIG. 1) has a pronounced and intense sandalwood odor. This is all the more surprising since according to the general state of knowledge, only compounds which contain 14 or more carbon atoms should have sandalwood aromas (G. Ohloff, *Fortschr. Chem. Forsch.*, Vol. 12/2, p. 213, 1969).

Therefore, campholenal (1) can be used as a starting material; it permits the construction of suitable side chains, and it can also be obtained in large amounts according to well-known methods (e.g. L. C. King and H. Farber, *J. Org. Chem.* 26, 326, 1961) by rearrangement of α-pinene epoxide. Also, the enantiomeric forms of campholenal result from the naturally occurring optical antipodes of α-pinene, which can be used individually or as a mixture. The synthesis of the side chains is carried out by well-known methods (FIGS. 1 and 2), and results in homogeneous products, in contrast to U.S. Pat. No. 4,052,341.

DETAILED DESCRIPTION OF PREFERRED EMBODIMENTS

The unsaturated compounds of Formula I can be prepared easily by the Wittig Reaction of 1 with α-bromoalkanoic esters with 3 to 5 carbon atoms in the alkanoic acid portion (including the carboxyl group), preferably the ethyl esters, by well-known procedures (*Helv. Chim. Acta* 40, 1242, [1957]).

The phosphineylides needed for Wittig Reaction can be prepared in a known manner by the action of strong bases on the phosphonium salts obtained by the reaction of α-haloalkanoic esters (halo=chloro, bromo, iodo) with triphenylphosphine (review article: Tripett, *Quart. Reviews,* Vol. 17, p. 406 [1963]).

As usual, aliphatic or aromatic hydrocarbons (e.g. hexane, octane, cyclohexane, benzene, toluene, and xylene), their halogenation products, and alcohols (e.g. methanol, ethanol, isopropanol, butanols, hexanols, cyclohexanol, cyclooctanol), glycols, and ethers (e.g. diisopropyl ether, ethylene glycol dimethyl ether, tetrahydrofuran, dimethyltetrahydrofuran, and dioxane), or their mixtures can be used as solvents for the preparation of the phosphineylides and for carrying out the Wittig Reaction. Polar aprotic solvents such as methanol, ethanol, formamide, dimethylformamide, N-methylpyrrolidone, hexamethyl phosphoramide, acetonitrile, and dimethyl sulfoxide, or their mixtures, are especially suitable. The process can also be carried out in the presence of water.

To carry out the Wittig Reaction, esters of α-halo fatty acids (halo=chloro, bromo, iodo) are caused to react with stoichiometric quantities of a strong base, to give the particular phosphoranylidenes. Suitable bases are alkali hydroxides, alkali hydrides, alkali amides, alkali and alkaline earth alkoxides, phenyllithium, or butyllithium. The phosphineylides thus obtained are caused to react with campholenal in the solvents mentioned at temperatures of 10°–40° C.

The Witting Reaction can also be carried out in a single step, by dissolving the phosphonium salt and approximately stoichiometric quantities of campholenal in a solvent, treating the approximately stoichiometric amounts of a strong base, and holding the mixture at temperatures of 10°–40° C. for one to two hours.

Figure 1:
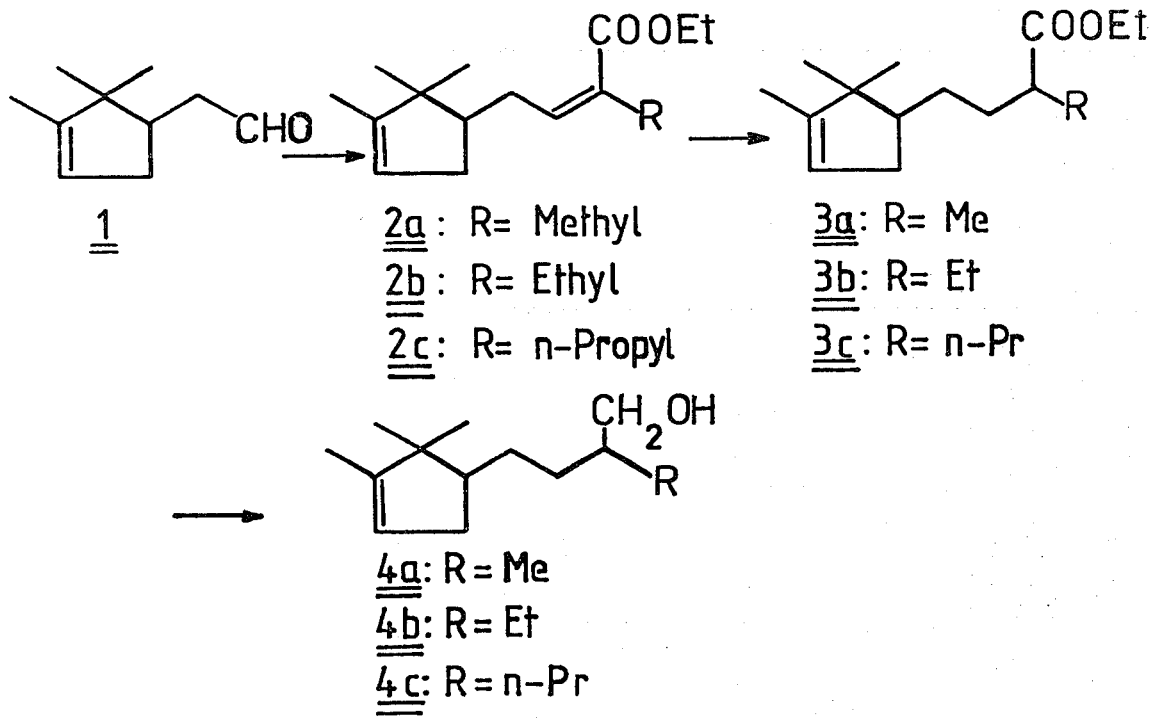
FIG. 1 shows one reaction scheme for the production of compounds in accordance with the present invention.

The compounds 2a, b, and c, of FIG. 1 were prepared in this way, and 3a, b, and c, were obtained from these compounds by catalytic hydrogenation. Reduction of the esters, for example with alkali metals or alkaline earth metals in alcohols, or with mixed hydrides of metals of the first and third major groups, provided the carbinols 4a, b, and c, which have an intense sandalwood odor.

The hydrogenation was accomplished in a known manner with the use of transition metal catalysts, preferably platinum, (Adams catalyst, Pt or activated charcoal), palladium (on activated charcoal), or Raney nickel in a neutral medium, preferably methanol or ethyl acetate at temperatures of 10°–80° C., and pressures of 1–30 atm, preferably 20°–40° C. and 1–5 atm.

The ester reduction is accomplished by Bouveault-Blanc Reduction, using alkali metals or alkaline earth metals in alcohols, preferably sodium in amyl alcohol, or using mixed hydrides of the elements of the first and third major groups in a polar aprotic solvent, preferably with Li[AlH$_4$] in diethyl ether.

The methods of reduction mentioned and just discussed, and the catalytic hydrogenation, as already mentioned, are known as such and require no detailed explanation. However, they are mentioned again in the examples of preparation which follow later.

Figure 2:
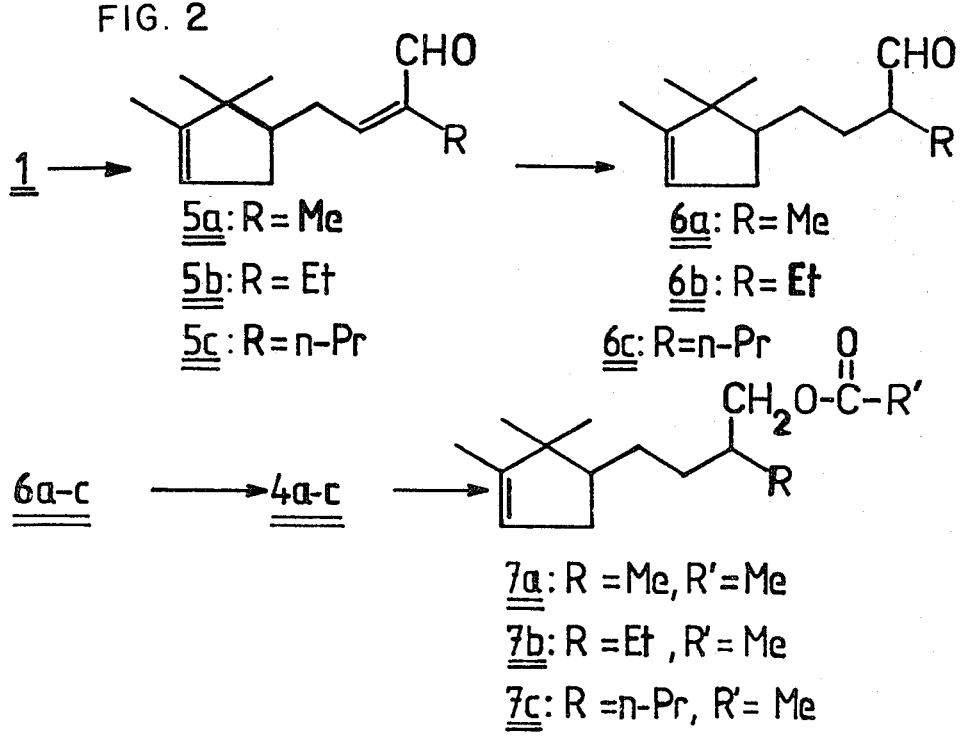
FIG. 2 shows a second reaction scheme for the production of compounds in accordance with the present invention.

Another synthetic route proceeds from the base-catalyzed aldol condensation of 1 with aliphatic C$_3$ to C$_5$ aldehydes (FIG. 2). The unsaturated aldehydes 5a–c obtained in this way were converted by catalytic hydrogenation into 6a–c, and, by subsequent reduction, into the saturated carbinols 4a–c. These reactions also are well known as such.

Alkali hydroxides or alkali alkoxides, preferably sodium hydroxide or sodium ethoxide, are used as bases for aldol condensations of campholenal with aliphatic aldehydes; boric anhydride is also suitable. Alcohols, preferably methanol or ethanol, serve as the solvent.

The aldehydes 6a–c are also accessible by the reaction of 1 with substituted vinyl alkyl ethers with BF$_3$ catalysis (in analogy with S. Satsumabayshi, K. Nakajo, R. Soneda, and S. Motoki, *Bull. Chem. Soc. Japan* 43, 1586 [1970]).

The alcohols 4a–c were esterified with acetic acid in a known manner to give the acetoxymethyl compounds 7a–c.

Suitable IR, NMR, and mass spectra are available for the new compounds (2a–c→7a–c).

The compounds of the general formula I excel in their special aromatic properties, in particular with mildly woody (4a–c), green woody (6a–c), and also perhaps somewhat resinous, fruity, ester-like shades of odor (7a–c). Above all, the alcohols 4a–c excel in their sometimes intense sandalwood odors; thus, 4a exceeds the structurally analogous 3-methyl-5-(2,2,3-trimethylcyclopent-3-ene-1-yl)pentene-2-ol (U.S. Pat. No. 4,052,341) in the odor intensity and therewith also in their strength in compositions. Compounds of the general formula I can accordingly be used as perfumes and as components of fragrance compositions such as perfumes and perfume bases, or for the perfuming of cosmetic and industrial products of all types.

The following examples illustrate the preparation of the compounds pursuant to the invention.

PREPARATIVE EXAMPLE 1

1-(3-carbethoxybut-2-enyl)-2,2,3-trimethylcyclopent-3-ene (2a)

150 g (1 mole) of campholenal (1) and 470 g of (2-carbethoxyethylidene)triphenylphosphorane in 4.5 L of benzene were stirred under N$_2$ for 6 hours at the boiling point. After cooling, washing with water, and distilling off the benzene, the residue was taken up in petroleum ether and filtered. From the crude product remaining after removal of the solvent by distillation (210 g of yellow oil), 176 g (75%) of 2a, $b_{0.8}105°–108°$ C., was obtained by fractional distillation.

PREPARATIVE EXAMPLE 2

1-(3-carbethoxybutyl)-2,2,3-trimethylcyclopent-3-ene (3a)

A solution of 100 g (0.42 mole) of 2a in 300 mL of methanol was hydrogenated under standard conditions with 5 g of Raney nickel (ca. 10 hours). Filtration, distillation of the solvent, and fractionation yielded 94 g (94%) of 3a, $b_{0.7}92°–95°$ C.

PREPARATIVE EXAMPLE 3

1-(3-hydroxymethylbutyl)-2,2,3-trimethylcyclopent-3-ene (4a)

50 g of 3a in 200 mL of absolute ether was added dropwise at 15° C. to a slurry of 9 g of Li[AlH$_4$] in 250 mL of absolute ether. After four hours of stirring at room temperature, 20 mL of glacial acetic acid was added. The reaction was poured onto ca. 300 g of ice, processed and fractionated. The yield was 32 g (83%) of 4a, b$_{0.8}$96°–99° C.

PREPARATIVE EXAMPLE 4

1-(3-formyl-2-alkanyl)-2,2,3-trimethylcyclopent-3-enes (5a–c)

At ca. 0° C., 368 g (2.4 moles) of campholenal (1) was added in each case to suspensions of 17 g of sodium ethoxide in 450 mL of methanol. To each mixture was added dropwise over a period of one hour, ca. 5 moles of the aldehyde (propionaldehyde, butyraldehyde, and n-valeraldehyde) (internal temperature, 40° C.). After one hour of stirring at room temperature, acidification with 50 mL of glacial acetic acid in each case, distillation of the methanol, processing, and fractional distillation, there remained 60 to 80% of the corresponding aldehyde (5a–c).

PREPARATIVE EXAMPLE 5

1-(3-formyl-2-alkyl)-2,2,3-trimethylcyclopentenes (6a–c)

In each case, 100 g of the aldehyde 5a–c (from Preparative Example 4) was hydrogenated in 200 mL of methanol with 5 g of Raney nickel for 3 hours under standard conditions. Filtration and distillation of the methanol provided 80 to 90% of the aldehydes 6a–c. On carrying out the hydrogenation at elevated pressure, preferably 20–60 atm, further reduction to 4a–c took place.

PREPARATIVE EXAMPLE 6

1-(3-hydroxymethyl-2-alkyl)-2,2,3-trimethylcyclopent-3-enes (4a–c)

To solutions of 150 g of the aldehydes 6a–c in each case (from Preparative Example 5) in 100 mL of ethanol, solutions of 38 g of sodium borohydride and 0.6 g of NaOH in 75 mL of water were added dropwise at 35°–40° C. over a period of 30 min. After 3 hours of stirring at room temperature and distillation, the alcohols 4a–c were present in yields of 75–85%.

The following examples show the use of the compounds pursuant to the invention.

EXAMPLE 7

| Perfume oil with sandalwood odor | |
|---|---|
| Linalool | 120 g |
| Oak moss extract, 50% in diethyl phthalate (DEP) | 100 g |
| Geranium oil bourbon | 100 g |
| Storax extract | 100 g |
| Coumarin | 70 g |
| Lavandin oil | 65 g |
| Amyl salicylate | 50 g |
| Benzyl salicylate | 50 g |
| Heliotropin | 50 g |
| Hydroxycitronellal | 50 g |
| Musk ambrette | 50 g |
| Musk ketone | 50 g |
| Neryl acetate | 35 g |

| -continued | |
|---|---|
| Perfume oil with sandalwood odor | |
| Patchouli oil | 30 g |
| Eugenol | 20 g |
| | 940 g |

An addition of 60 g of compounds 4a or 4b to the above mixture endows the resulting perfume oil with a natural persistent sandalwood odor.

EXAMPLE 8

| Perfume oil with aldehydic woody note | |
|---|---|
| Bergamot oil | 150 g |
| α-hexylcinnamaldehyde | 100 g |
| p-isopropyl-α-methylcinnamaldehyde | 100 g |
| Vetiveryl acetate | 100 g |
| Calarene epoxide | 70 g |
| Methylionone | 70 g |
| Musk ketone | 50 g |
| Isobutylquinoline 1%/DEP | 45 g |
| Citronellol | 35 g |
| Undecylenaldehyde 10% in DEP | 30 g |
| Styrenyl acetate 10% in DEP | 30 g |
| Galbanum oil | 20 g |
| Cyclopentadecanolide | 20 g |
| Oak moss extract | 15 g |
| Elemi oil | 15 g |
| Iris extract | 15 g |
| Tonka bean extract | 15 g |
| Ylang-Ylang oil | 15 g |
| Decanal 10% in DEP | 10 g |
| Methylnonylacetaldehyde 10% in DEP | 10 g |
| Isoeugenol | 10 g |
| Neryl acetate | 10 g |
| Absolute oil of orange blossom | 5 g |
| | 940 g |

An addition of 60 g of compound 4a brings about a very desirable intensification of the woody background odor and provides a perfume oil with natural emanation.

EXAMPLE 9

| Perfume oil with heavy balsam note | |
|---|---|
| Phenylethyl alcohol | 180 g |
| Patchouli oil | 129 g |
| Bergamot oil | 90 g |
| Methylionone | 60 g |
| Musk ketone | 60 g |
| α-hexylcinnamaldehyde | 50 g |
| Eugenol | 40 g |
| Lavender oil | 40 g |
| Benzyl salicylate | 30 g |
| Hydroxyisohexyltetrahydrobenzaldehyde | 70 g |
| Ethylvanillin 10% in DEP | 30 g |
| Siam benzoin - resinoid | 25 g |
| Phenylethyl acetate | 25 g |
| Benzyl acetate | 25 g |
| Coumarin | 25 g |
| Geranium oil bourbon | 25 g |
| Peru balsam oil | 20 g |
| Ethylene brassylate | 15 g |
| Isoeugenol | 10 g |
| German camomile oil | 10 g |
| | 950 g |

The addition of 50 g of compound 4b rounds off the perfume oil in a natural manner and imparts to the balsam fragrance components a strong fresh background scent.

EXAMPLE 10

| Perfume oil with flowery fragrance | |
| --- | --- |
| Citronellol | 100 g |
| Phenylacetaldehyde, 10% in phenylethyl alcohol | 100 g |
| Ethylene brassylate | 85 |
| α-amylcinnamaldehyde | 80 g |
| Hydroxycitronellal | 80 g |
| α-ionone | 80 g |
| Anise alcohol | 60 g |
| Heliotropin | 50 g |
| Cinnamyl alcohol | 50 g |
| Methyl octynoate, 10% in DEP | 50 g |
| Phenylethyl alcohol | 55 g |
| Phenylethyl acetate | 45 g |
| Nerol | 40 g |
| Methyl naphthyl ketone | 35 g |
| Monomenthadienyl formate | 30 g |
| Anisyl acetate | 20 g |
| Citronellyl nitrile | 15 g |
| | 975 g |

In each case, 25 g of the compounds 4a, 4b, 4c, added to this mixture, impart a natural emanation to the flower-like aroma, with simultaneous fixation.

EXAMPLE 11

| Perfume oil of the aldehydic cypress type | |
| --- | --- |
| Vetiveryl acetate | 200 g |
| Bergamot oil | 110 g |
| Calarene epoxide | 110 g |
| Lemon oil | 60 g |
| Linaloyl acetate | 55 g |
| α-hexylcinnamaldehyde | 50 g |
| Hydroxyisohexyltetrahydrobenzaldehyde | 50 g |
| Phenylethyl alcohol | 50 g |
| Oak moss extract | 40 g |
| Musk ambrette | 40 g |
| Benzyl acetate | 30 g |
| Undecylenal, 10% in DEP | 25 g |
| Methylionone | 40 g |
| Neroli oil | 20 g |
| Lavender oil | 20 g |
| Citronellyl propionate | 20 g |
| Citronellol | 20 g |
| Coumarin | 15 g |
| Dodecanal 10% in DEP | 15 g |
| | 970 g |

If 30 g of compound 6a is added to this mixture, an immediate intensification of the aldehydic fresh cypress odor is noted, which also undergoes a substantial fixation from this addition.

EXAMPLE 12

| Perfume with lily of the valley odor | |
| --- | --- |
| Hydroxycitronellal | 200 g |
| Phenylethyl alcohol | 200 g |
| α-hexylcinnamaldehyde | 200 g |
| Linalool | 100 g |
| Rhodinol | 80 g |
| Rosewood oil | 25 g |
| Geraniol | 20 g |
| Ylang-ylang oil | 15 g |
| Indole 10% in DEP | 10 g |
| Benzyl acetate | 10 g |
| Phenylacetaldehyde dimethyl acetal | 10 g |
| Oil of cinnamon, 10% in DEP | 10 g |
| Hydroxyisohexyltetrahydrobenzaldehyde | 30 g |
| Linaloyl acetate | 25 g |
| Heptanal, 10% in DEP | 5 g |
| | 940 g |

An addition of 60 g in each case of compounds 7a–c imparts a fresh fruity blossom character to the perfume oil, with great emanation.

It will be obvious to those skilled in the art that various changes may be made without departing from the scope of the invention and the invention is not to be considered limited to what is shown in the drawings and described in the specification.

What is claimed is:

1. A compound of the general formula:

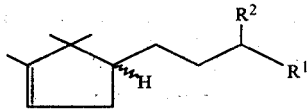

wherein R¹ represents a lower alkyl group with 1–3 carbon atoms and R² represents a hydroxymethyl, acetoxymethyl, or formyl group, and the wavy line signifies epimeric forms at carbon atom 1.

2. A compound in accordance with claim 1, wherein R¹ signifies a methyl, ethyl or n-propyl group.

3. A perfume composition comprising 1 to 10% of the compound of either of claims 1 or 2 and the remainder other perfume composition adjuvants.

* * * * *